US008736833B2

(12) United States Patent
Barea

(10) Patent No.: US 8,736,833 B2
(45) Date of Patent: May 27, 2014

(54) DEVICE AND METHOD FOR SENSING A CHANGE OF YARN FEED BOBBIN

(75) Inventor: Tiziano Barea, Busto Arsizio (IT)

(73) Assignee: BSTR International S.p.A., Olgiate Olona (Varese) (IT)

(*) Notice: Subject to any disclaimer, the term of this patent is extended or adjusted under 35 U.S.C. 154(b) by 0 days.

(21) Appl. No.: 13/995,393

(22) PCT Filed: Jun. 27, 2012

(86) PCT No.: PCT/IB2012/001288
§ 371 (c)(1),
(2), (4) Date: Jun. 18, 2013

(87) PCT Pub. No.: WO2013/005087
PCT Pub. Date: Jan. 10, 2013

(65) Prior Publication Data
US 2014/0110523 A1    Apr. 24, 2014

(30) Foreign Application Priority Data
Jul. 6, 2011   (IT) ............... MI2011A1252

(51) Int. Cl.
*G01N 21/00* (2006.01)
*B65H 75/00* (2006.01)
*G01N 27/447* (2006.01)

(52) U.S. Cl.
CPC .......... *B65H 75/00* (2013.01); *G01N 27/44791* (2013.01)
USPC .................... 356/238.1; 356/238.2

(58) Field of Classification Search
CPC .. B65H 2701/31; B65H 49/12; B65H 63/086; B65H 67/063; B65H 2557/65; B65H 57/22; B65H 59/06; B65H 67/068; B65H 67/069
See application file for complete search history.

(56) References Cited

U.S. PATENT DOCUMENTS

| 7,370,464 | B2 * | 5/2008 | Barea | 57/261 |
| 7,773,225 | B2 * | 8/2010 | Barea | 356/429 |
| 2008/0225305 | A1 | 9/2008 | Barea | |

FOREIGN PATENT DOCUMENTS

| BE | 1000331 A4 | 10/1988 |
| DE | 19544632 A1 | 6/1997 |
| EP | 0459553 A1 | 12/1991 |

OTHER PUBLICATIONS

International Search Report issued in PCT/IB2012/001288 to BAREA dated Dec. 14, 2012.

* cited by examiner

*Primary Examiner* — Michael P Stafira
(74) *Attorney, Agent, or Firm* — Novak Druce Connolly Bove + Quigg LLP

(57) ABSTRACT

A device for sensing the change of feed bobbin for a yarn fed to a textile machine and originating from a first bobbin or a second bobbin connected together in head-tail manner includes at least one first sensor and one second sensor at a passage section of a support body, a control unit associated with the first sensor and second sensor. The first sensor and the second sensor generates first and second presence signals when the yarn unwound from the first bobbin or from the second bobbin passes in front of the first sensor or second sensor. The control unit receiving as input the first and/or second presence signal to generate at least one output signal representative of the first bobbin or of the second bobbin on the basis of the first or second presence signal.

18 Claims, 4 Drawing Sheets

US 8,736,833 B2

DEVICE AND METHOD FOR SENSING A CHANGE OF YARN FEED BOBBIN

CROSS-REFERENCE TO RELATED APPLICATIONS

This is a §371 National Stage Application of International Application No. PCT/IB2012/001288 filed on 27 Jun. 2012, claiming the priority of Italian Patent Application No. MI2011A001252 filed on 6 Jul. 2011.

FIELD OF THE INVENTION

The present invention relates to a device and method for sensing the change of feed bobbin for yarn fed to a textile machine in accordance with the introduction to the main claim.

In particular, the present invention finds application in that yarn feed to textile machines achieved by connecting a first and a second bobbin together by head-tail connection, when the depletion of one bobbin and the commencement of the next bobbin has to be sensed. In this respect, in a head-tail connection the tail portion of the yarn of the first bobbin is connected, for example knotted, to the head portion of the successive second bobbin, such that yarn feed to the textile machine is maintained continuous on depletion of the first bobbin, i.e. after the "bobbin change".

BACKGROUND OF THE INVENTION

Devices for sensing yarn bobbin change are known. These known devices present a sensitive zone in which the connection portion between the yarn of one bobbin and the yarn of the next bobbin is housed.

Frequently, the connection portion is maintained within the sensitive zone by the use of yarn braking grippers, to prevent this portion from inadvertently escaping, to hence generate a false reading.

When the bobbin is approaching depletion, this connection portion is dragged towards the textile machine, hence leaving the sensitive zone. Suitable sensors, for example capacitive, optical or piezoelectric, sense this exit and indicate that the bobbin change, also known as "head-tail event", has taken place.

Devices of the known type present however certain drawbacks.

Firstly, sensing the head-tail event is exclusively related to sensing the moment in which the yarn connection portion is dragged out of the sensitive zone of the device. Because of the high speed with which the yarn is fed to the textile machine, it can frequently happen that the device is unable to detect that single instantaneous event, and hence sense it.

Moreover, the frequent need to reposition the yarn braking grippers makes installation of such devices on textile machines substantially more complicated.

Again, the yarn braking grippers exert a braking action on the yarn which, at the moment of the head-tail event, must be counteracted and overcome, risking yarn breakage.

SUMMARY OF THE INVENTION

In this context, the technical aim at the basis of the present invention is to propose a device and method for sensing the change of yarn feed bobbin in a textile machine which overcomes the aforestated drawbacks of the known art.

A particular object of the present invention is to provide a device and method for sensing the change of yarn feed bobbin in a textile machine in which the feed takes place by head-tail connection of at least two bobbins, which is able to securely and reliably intercept the head-tail event.

A further object of the present invention is to propose a device and method for sensing the change of yarn feed bobbin in a textile machine which are able to sense the head-tail event without altering the yarn processing conditions.

The stated technical aim and the specified objects are substantially attained by a device and method for sensing the change of yarn feed bobbin in a textile machine, comprising the technical characteristics stated in one or more of the accompanying claims.

BRIEF DESCRIPTION OF THE DRAWINGS

Further characteristics and advantages of the present invention will be more apparent from the indicative and hence non-limiting description of a preferred but non-exclusive embodiment of a device for sensing the change of yarn feed bobbin in a textile machine, as illustrated in the accompanying drawings, in which.

DETAILED DESCRIPTION OF THE PREFERRED EMBODIMENTS

Figure 1:
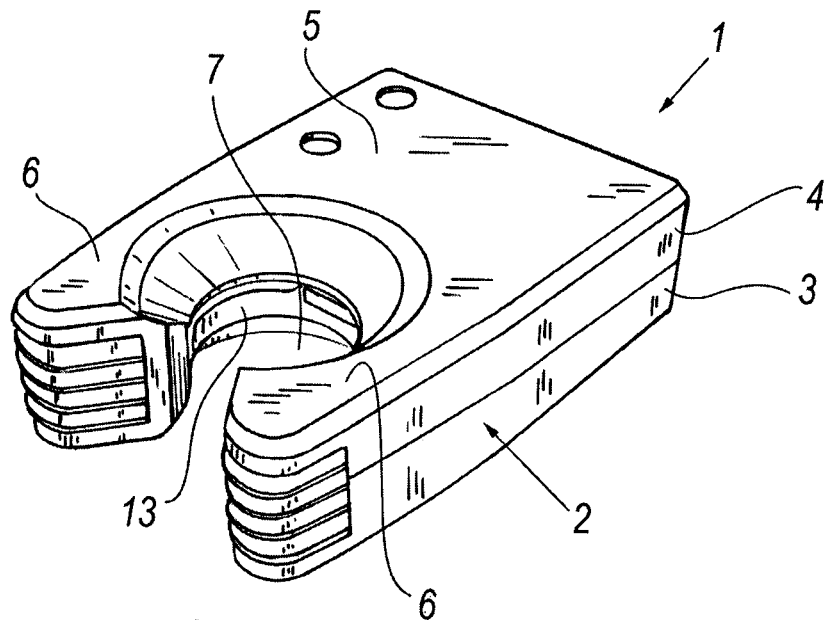
FIGS. 1 and 2 are respective perspective views of a device according to the present invention for sensing the change of yarn feed bobbin in a textile machine, in two respective angulations.
Figure 2:
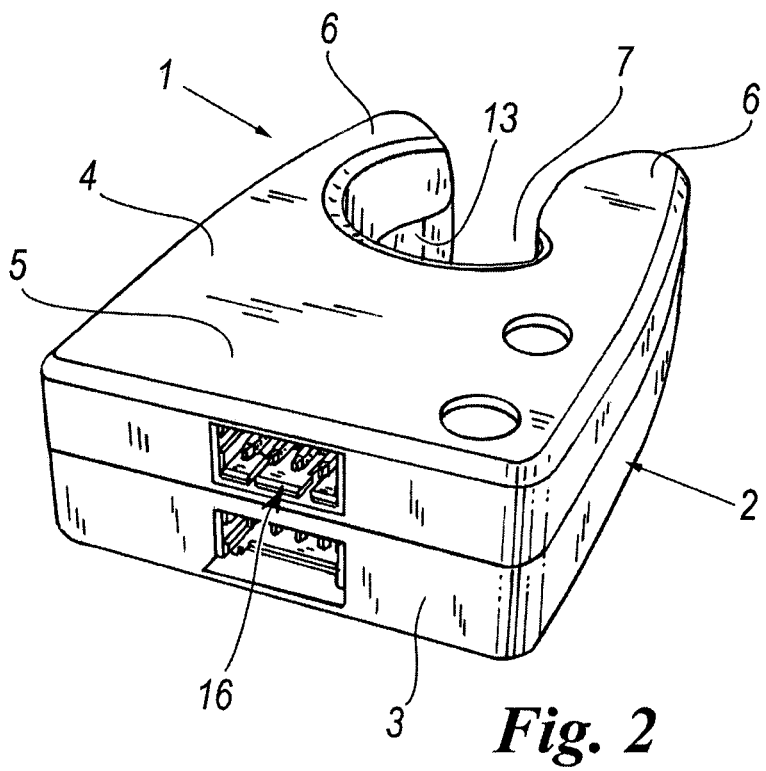

With reference to the accompanying figures, the reference numeral 1 indicates overall a device according to the present invention for sensing the change of yarn feed bobbin in a textile machine, said feed taking place by using two bobbins in head-tail connection.

In particular, the device 1 senses the end of the yarn originating from a first bobbin B1 and the commencement of the yarn originating from a second bobbin B2 connected together by said head-tail connection.

Figure 3:
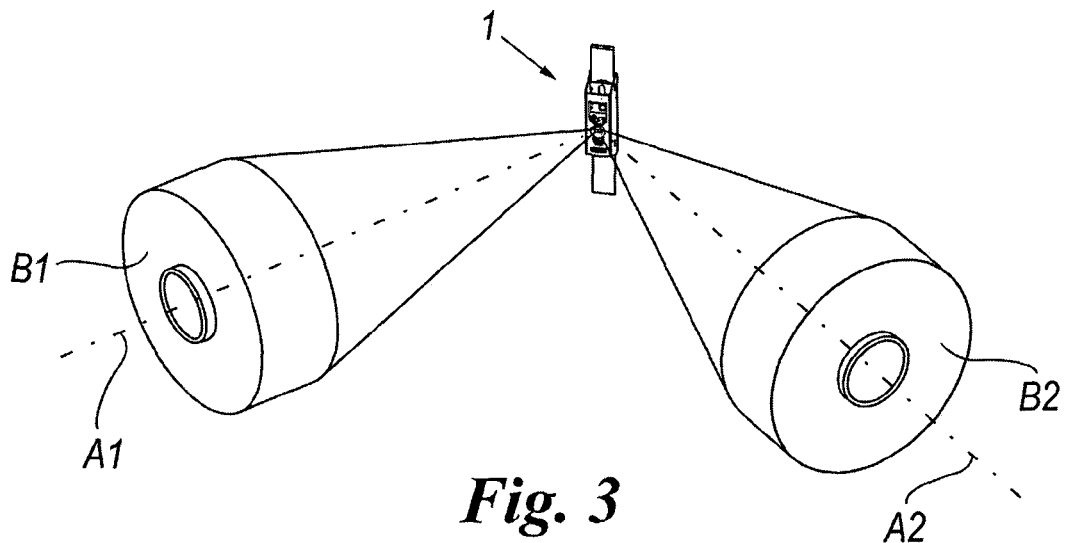
FIG. 3 is a perspective view of the device of FIGS. 1 and 2 and of the yarn feed bobbins.

It should be noted that the first bobbin B1 and the second B2 are disposed with their central axes A1, A2 mutually inclined (FIG. 3).

The device 1 comprises a support body 2 formed from two half-shells 3, 4 coupled together to form an internal compartment for containing the components which will be described hereinafter and connected together by clamping means (for example screws) which are not shown.

As illustrated, the support body 2 comprises a main portion 5 and two arms 6 which extend mutually opposing from the main portion 5. Between the arms 6 a passage section 7 is defined through which the yarn transits from the bobbins B1, B2 towards a textile machine (not shown).

According to the illustrated embodiment, the arms 6 are shaped such that the passage section 7 is substantially circular.

The device 1 generally comprises yarn sensing means 8, 9 defining at least one first sensing zone 8a and one second sensing zone 9a positioned in the yarn passage section 7.

The sensing means comprise at least one first sensor 8 and one second sensor 9 (for example a presence or proximity, optical, contact or other sensor) positioned at the passage section 7 and preferably opposite each other. In detail, the first sensor 8 and second sensor 9 are disposed in positions corresponding with said arms 6.

The first sensor 8 and second sensor 9 are arranged to generate respectively at least one first and at least one second presence signal representative of yarn passage in front of the first sensor 8 and the second sensor 9 respectively. In other words, the first sensor 8 and the second sensor 9 sense the presence of the yarn in respective mutually separate sensitive areas positioned at the passage section 7.

In a non-illustrated embodiment, the sensing means define a plurality of sensing zones. In this respect, the sensing means comprise a plurality of said sensors, each defining a corresponding sensing zone, to sense the presence of the yarn in other mutually separate positions, for example to identify three or more control zones for a process in which there are three or more head-tail connected bobbins.

It should be noted that during the unwinding of the yarn from the first bobbin B1 or second bobbin B2, the yarn undergoes a rotary movement on a conical surface having its base at the bobbin and its vertex at the passage section 7, and in particular in one of the two aforedefined sensitive zones. This movement is known as ballooning.

As the bobbins B1 and B2 are disposed with their central axes mutually inclined, when the first bobbin B1 is depleted and yarn withdrawal from the second bobbin B2 commences, the trajectory of the yarn in approaching the passage section 7 changes suddenly, passing for example from the sensitive area of the second sensor 8 to the sensitive area of the second sensor 9.

A control unit 10 is operatively associated with the first sensor 8 and second sensor 9 such as to receive as input the first and second presence signal. The control unit 10 also generates at least one output signal representative of that bobbin which is gradually unwinding. In other words, the output signal represents the identification of the first bobbin B1 or of the second bobbin B2. In the preferred embodiment shown in the drawings, the first sensor 8 and second sensor 9 are of photo-optic type.

In this respect, the first sensor 8 and second sensor 9 comprise respective light emitter elements 11 for illuminating the yarn in transit, and at least one receiver element 12 to receive a portion of this light (a part of the light is in fact absorbed/obscured and/or reflected by the yarn).

For example, such light emitter elements 11 can be LEDs (infrared, laser or visible light). Again for example, the receiver element 12 can be a photodiode, a phototransistor, a PSD, a CCD or others.

Figure 4:
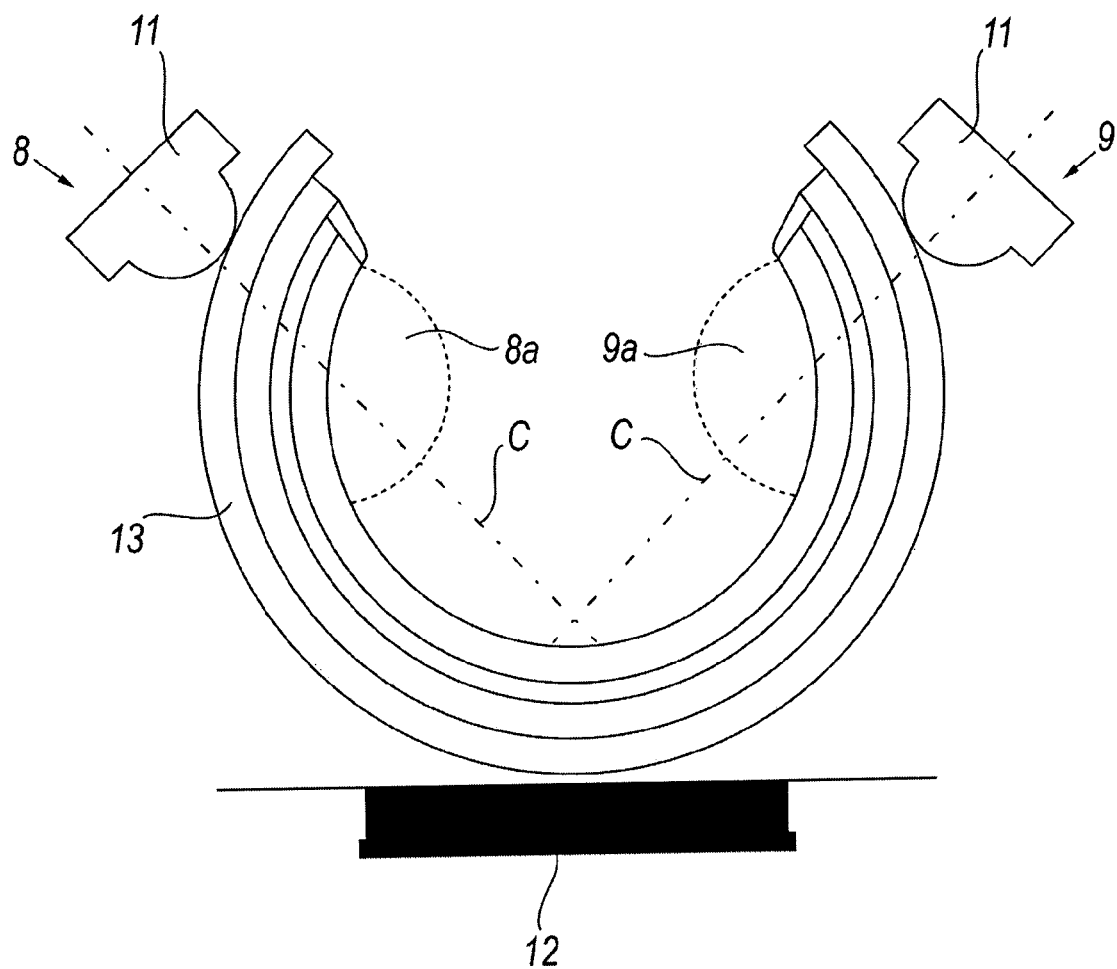
FIG. 4 is a schematic view of the device of FIGS. 1 and 2.
Figure 5:
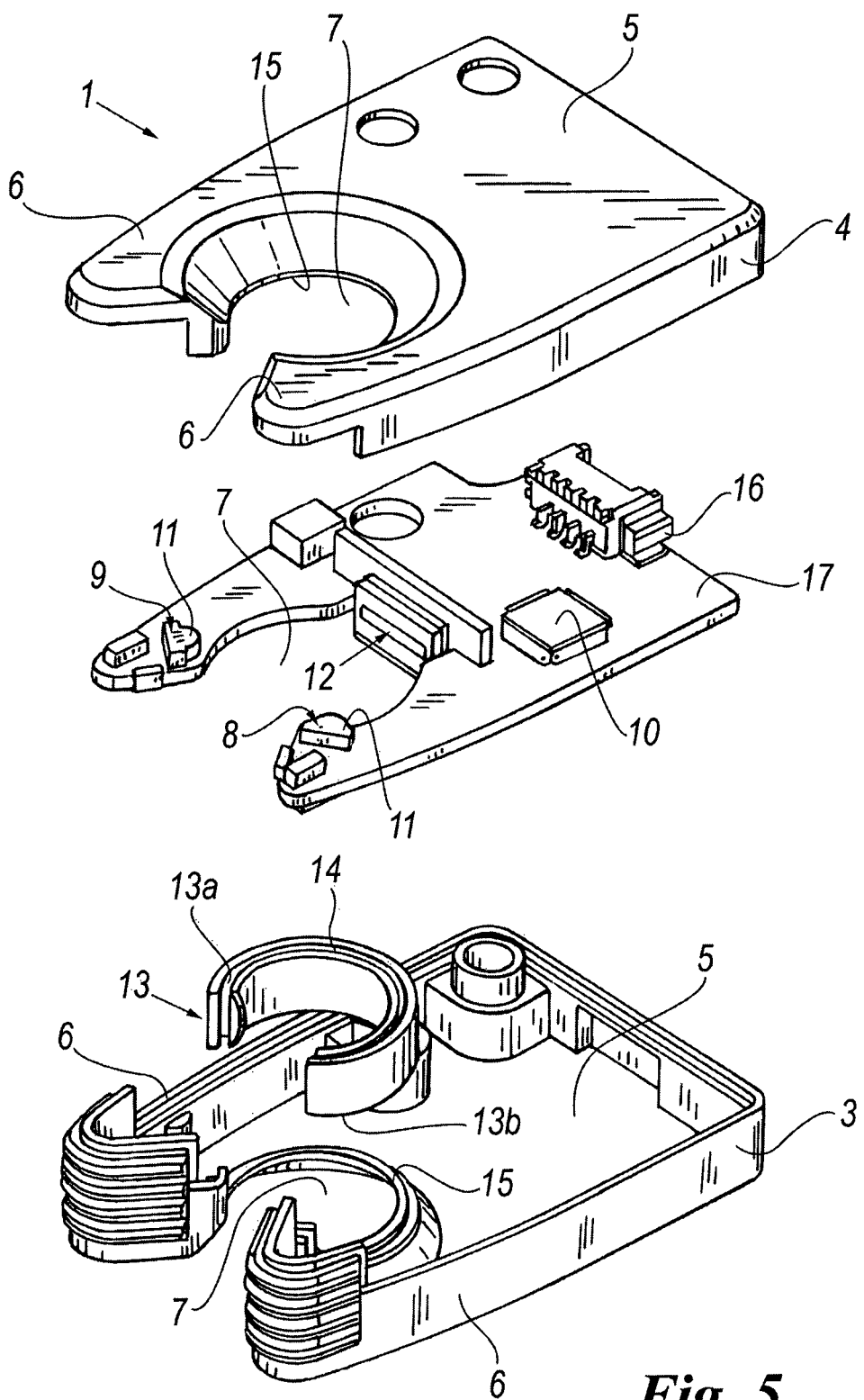
FIG. 5 is an exploded view of the device of FIGS. 1 and 2.

The light emitter elements 11 are disposed at an angle apart and preferably equidistant from the receiver element 12. The light emitter elements 11 are preferably disposed with their optical axes C incident or at least facing the light receiver element 12 (FIG. 4).

As shown, the device 1 comprises a single receiver element 12 which is shared by the first sensor 8 and second sensor 9.

In non-illustrated embodiments, each sensor 8, 9 comprises its own respective receiver element.

On receiving the light originating from the emitter element 11 of the first sensor 8 and second sensor 9 and obscured by the yarn, the receiver element 12 generates respectively the first and second presence signal.

Each emitter element 11, being activated simultaneously with the deactivation of the other emitter element 11, emits light in respective beams which are at least partly separated from each other. In other words, the emitter elements 11 generate light beams at the passage section 7 (for example conical) which do not intersect at least partly. Those regions of the passage section 7 occupied exclusively by only one of the beams emitted by the emitter elements 11 define said sensitive areas.

To distinguish with greater precision which of the sensitive zones is occupied at any given time by the yarn, the light emitter elements 11 can be activated in turn in presence to the first sensor 8 or to the second sensor 9 and in particular in correspondence with the respective sensitive areas.

In this manner, a succession of first or second presence signals is generated.

In this respect, the control unit 10 generates a command signal directed towards the light emitter elements 11 of the first sensor 8 and of the second sensor 9 to activate and deactivate them as required.

The control unit 10 is also operatively connected to the light receiver element 12 to receive a signal representative of light identification. By comparing the command signal with the signal representative of light identification, the control unit 10 generates the first or second presence signal which identifies the presence of the yarn in front of the first sensor 8 or second sensor 9.

On this basis the control unit 10 generates the change-over signal representative of the change in origin of the yarn from the first bobbin B1 to the second bobbin B2, and vice-versa. In other words, when the so-called head-tail event occurs, the control unit 10 generates the change-over signal.

In greater detail, when the succession of first presence signals terminates and the succession of second presence signals commences, the control unit 10 generates the change-over signal representative of the change in origin of the yarn from the first bobbin B1 to the second bobbin B2.

Likewise, when the succession of second presence signals ceases and the succession of first presence signals is activated, the control unit 10 generates the change-over signal representative of the change in origin of the yarn from the second bobbin B2 to the first bobbin B1.

It should be noted that if the control unit 10 does not sense either first or second presence signals, it generates a stop signal representative of the absence of yarn in the passage section 7 due, for example, to its breakage.

If the control unit 10 receives both first and second presence signals at the same time, it generates an irregularity signal representative of a state of irregular operation which needs checking by an operator.

It should be noted that in alternative embodiments, not shown, the first sensor 8 and second sensor 9 can also be of different type. For example, the first sensor 8 and second sensor 9 can be capacitive, piezoelectric, strain gauge or other element types arranged to define on the support body 2 at least two separate sensitive areas.

The device 1 also comprises notification means (not shown) operatively associated with the control unit 10 to acquire the change-over signal and/or the stop signal and/or the irregularity signal and to generate an acoustic or visual warning signal to inform a user regarding the operative state of the yarn feed to the textile machine.

In another possible alternative embodiment, instead of operating by obscuring (transmitter and receiver oppose each other to determine a beam which is obscured by the yarn), the optical sensors could operate by reflection, in which case the transmitter and receiver would be close together and the light received by the receiver would be that reflected by the yarn.

These notification means can for example be a plurality of LEDs which are lit on the basis of the operative state to be indicated, or a screen, or others.

These notification means can be integrated into the support body 2 or be separate and distinct.

The device 1 also comprises a connector 16 connected at least to the control unit 10. This connector 16, in addition to supplying the necessary electrical voltage for the operation of the control unit 10 and of the entire device 1, enables signals to leave and enter. For example, the change-over signal and/or the stop signal can leave via the connector 16.

The connector 16 can be used to connect the device 1 to the textile machine and in particular to its electronic control system, for example via a serial line, by which to programme any operating parameters (sensitivity, delay, . . . ) and/or to read the state of each sensor, these data being recorded in a database of the machine computer or of an external PC (yarn absent or head-tail event), to hence enable complete tracing of the finished product, by associating the bobbin of origin with it. For example, in this situation the stop signal can be transferred to the textile machine to enable it to be halted or can be indicated to an operator who then replaces the depleted bobbin to prevent the process from stopping.

The device 1 also comprises a support panel 17 disposed between the half-shells 3, 4 of the support body 2 and on which the first sensor 8 and the second sensor 9, the control unit 10 and the connector 16 are disposed. In detail, the support panel 17 is clamped between the half-shells 3, 4 to maintain it in a stable position.

The device 1 also comprises a thread guide member 13 disposed between the arms 6 of the support body 2 and defining the passage section 7.

The thread guide member 13 enables the yarn to slide on it without remaining entangled or torn.

Advantageously, the first bobbin B1 and the second bobbin B2 are orientated such that the yarn unwinding from them is always in contact with the thread guide member 13 at the first sensor 8 and at the second sensor 9.

The thread guide member 13 is enclosed between the half-shells 3, 4 and at least partially closes said compartment within the main body 2.

In detail, the thread guide member 13 presents two opposing edges 13a, 13b presenting respective recesses 14 intended to be occupied by shoulders 15 provided on the half-shells 3, 4 of the support body 2, to ensure stable connection.

In accordance with the shape of the passage section 7, the thread guide member 13 presents a substantially annular shape. In detail, the thread guide member 13 is of open ring shape. In a variant, the thread guide member 13 has other shapes, such as a closed ring, or forms an integral part of the textile machine.

The thread guide member 13 is formed of light transparent material. This is necessary as both the light emitter elements 11 and the light receiver element 12 are inside the support body 2.

Preferably, the thread guide member 13 is made of ceramic material such as alumina ceramic, zirconia ceramic or sapphire, synthetic material or similar materials.

Alternatively, the thread guide member 13 can be made of plastic material, such as nylon, polycarbonate and others, or glass.

Figure 6:
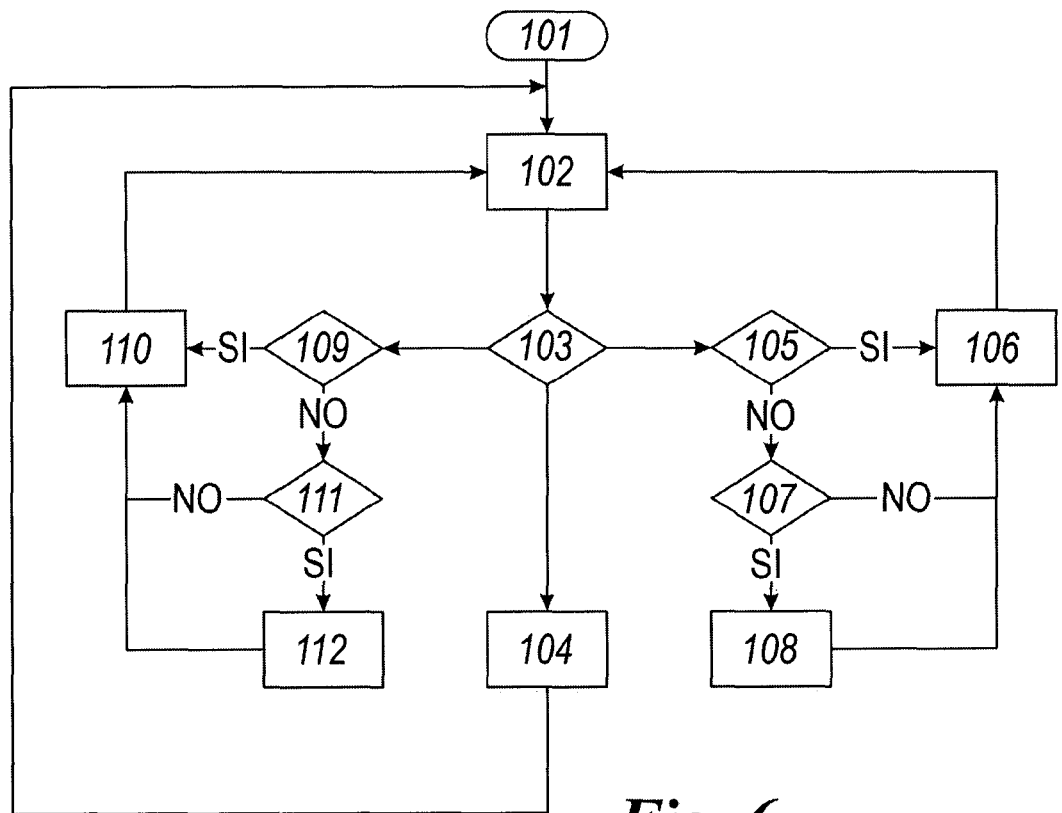
FIG. 6 is a block diagram relative to the operation of the device according to the invention.

The operation of the device 1 of the present invention will now be described in detail with reference to the flow diagram shown in FIG. 6.

The operation of the device 1 commences with an initialization stage (block 101) during which the process control variables are set.

Next, during a control stage (block 102) the light emitter elements 11 are lit alternately and the signal representative of light interception is collected by the light receiver element 12.

It should be noted that, during this stage, the duration of the periods for which the light emitter elements 11 remain lit or extinguished can be fixed or be programmable, being for example a function of the system response time. Again, this duration can be equal for both the light emitter elements 11 or be different. For example, it could be advantageous to prolong the determination of which sensing zone is occupied by the yarn in order to accelerate any detection of yarn breakage.

This control is carried out by the control unit 10.

This is followed by a stage of verification that the yarn is travelling (block 103).

In other words, the control unit 10 verifies whether at least one from the first sensor 8 and second sensor 9 senses yarn transit.

If neither the first nor the second presence signal is detected, the control unit 10, after a predetermined waiting time, generates the stop signal, interpreting this situation as a yarn breakage (block 104).

In that case the control unit 10 returns to waiting prior to the stage represented by block 102, ready to carry out the next control cycle after restarting the textile machine and restarting the yarn feed.

During the verification carried out under block 103, if the control unit 10 receives the first presence signal (i.e. in which the yarn travels in the vicinity of the first sensor 8), a verification is started represented by the block 105.

During this verification, the control unit 10 verifies whether the yarn also travelled in presence to the first sensor 8 during the preceding control cycle.

If positive, the control unit 10 updates the travel state by confirming it (block 106) and returns to block 102 to carry out a new control cycle, having verified that there has been no head-tail event.

If negative, the control unit 10 verifies whether the yarn travelled in presence to the second sensor 9 during the preceding control cycle (block 107).

If negative (i.e. if the yarn did not travel in presence to the second sensor 9), the control unit 10 updates the travel state by confirming it (block 106) and returns to block 102 to carry out a new control cycle.

If positive (i.e. if the yarn did travel in presence to the second sensor 9), the control unit 10 generates the change-over signal, having sensed a head-tail event, with change from the second bobbin B2 to the first bobbin B1 (block 108). In that case, after updating the travel state (block 106), the control unit 10 returns to block 102 to carry out a new control cycle.

Again during the verification carried out under block 103, if the control unit 10 receives the second presence signal (i.e. in which the yarn travels in the vicinity of the second sensor 9), a verification is started represented by the block 109.

During this verification, the control unit 10 verifies whether the yarn also travelled in presence to the second sensor 9 during the preceding control cycle.

If positive, the control unit 10 updates the travel state by confirming it (block 110) and returns to block 102 to carry out a new control cycle, having verified that there has been no head-tail event.

If negative, the control unit 10 verifies whether the yarn travelled in presence to the first sensor 8 during the preceding control cycle (block 111).

If negative (i.e. if the yarn did not travel in presence to the first sensor 8), the control unit 10 updates the travel state by confirming it (block 110) and returns to block 102 to carry out a new control cycle.

If positive (i.e. if the yarn did travel in presence to the first sensor 8), the control unit 10 generates the change-over signal, having sensed a head-tail event, with change from the first bobbin B1 to the second bobbin B2 (block 108). In that case, after updating the travel state (block 110), the control unit 10 returns to block 102 to carry out a new control cycle.

The invention attains the proposed objects and provides important advantages.

By using two separate sensors which sense the yarn position, the device for sensing the change of yarn feed bobbin according to the present invention enables it to be precisely and reliably determined from which of the two bobbins the yarn has been withdrawn at any given time.

Consequently, when after a head-tail event, i.e. after one bobbin has terminated and the next bobbin has commenced, the yarn modifies its trajectory in approaching the device 1, this modification is readily sensed to indicate the head-tail event, the event being identified by constant analysis of the travel state of the yarn intercepted by two sensors 8 and 9 and not by means of a single event as in state of the art solutions.

Moreover advantageously, the sensing of the head-tail event cannot be influenced by the yarn advancement velocity.

It should also be noted that the sensing of the head-tail event implies no modification to the operative conditions of the textile machine nor of the yarn feed to the machine.

In particular, with the device for sensing the change of yarn feed bobbin there is no risk of imposing additional tensions on the yarn and even less of causing its breakage or tearing.

Advantageously, the device of the present invention is of very simple construction and can also be easily mounted on textile machines without the need for special interventions.

The invention claimed is:

1. A device for sensing the change of feed bobbin for a yarn fed to a textile machine and originating from a first bobbin or a second bobbin connected together in head-tail manner, comprising
    a support body defining a passage section for a yarn,
    yarn sensing means comprising at least one first sensor and one second sensor which respectively define a first sensing zone and a second sensing zone positioned at said passage section,
    a control unit operatively associated with said sensing means to control the feed of said yarn to the textile machine,
    said sensing means arranged to generate corresponding first and second presence signals when the yarn unwound from the first bobbin or from the second bobbin passes through said first sensing zone or second sensing zone,
    said control unit arranged to receive said first and/or second presence signal as input and also arranged to generate at least one output signal indicating whether said yarn originates from said first bobbin or from said second bobbin on the basis of said first or second presence signal;
    said first sensor and second sensor comprising respective light emitter elements to illuminate said yarn in presence to said first sensor or said second sensor, and at least one receiver element;
    said light emitter elements being activatable in turn to illuminate said yarn exclusively in presence to said first sensor or said second sensor to generate a succession of first and second presence signals;
    wherein said control unit generates a change-over signal representative of the change in origin of said yarn from said first bobbin to said second bobbin when said first presence signals terminate and said second presence signals commence.

2. A device as claimed in claim 1, wherein, if said first and second presence signals are not received, said control unit for generating a stop signal representative of the absence of yarn in the passage section.

3. A device as claimed in claim 1, wherein said control unit for generating an irregularity signal if said first signals and second signals are received simultaneously.

4. A device as claimed in claim 1, wherein said sensing means comprise a plurality of said sensing zones to sense from which bobbin of a plurality of bobbins does the yarn originate.

5. A device as claimed in claim 1, wherein each light emitter element emits light in respective beams which are at least partially separated from each other.

6. A device as claimed in claim 1, further comprising change-over notification means operatively associated with the control unit to acquire said change-over signal and/or the stop signal and to generate a corresponding electrical, acoustic and/or visual warning signal.

7. A device as claimed in claim 1, wherein said support body comprises a main portion and two arms which extend mutually opposing from said main portion; said passage section being defined between said arms.

8. A device as claimed in claim 7, wherein said first sensor and second sensor are disposed in correspondence with said arms.

9. A device as claimed in claim 8, further comprising a thread guide member disposed between the arms and at least partly defining said passage section.

10. A device as claimed in claim 1, wherein said first sensor and second sensor are of piezoelectric, capacitive, strain gauge or contact type.

11. A device as claimed in claim 1, further comprising a connection for connecting said device to a textile machine, to programme at least one operating parameter and/or to read an intercepted state or event to save at least one information item in order to enable traceability of the finished product on the basis of the bobbin of origin.

12. A method for sensing the change of feed bobbin for a yarn fed to a textile machine and originating from a first bobbin or a second bobbin connected together in head-tail manner, by a device in accordance with claim 1, comprising:
    guiding the yarn originating from the first bobbin or second bobbin through the passage section at the first sensor or second sensor;
    activating said first sensor and said second sensor in turn to generate a succession of first or second presence signals when the yarn unwound from the first bobbin or from the second bobbin passes in front of said first sensor or second sensor and feeding said first or second presence signals to said control unit;
    generating by means of said control unit at least one output signal representative of the origin of said yarn from the first bobbin or from said second bobbin on the basis of said first or second presence signal;
    generating by means of said control unit a change-over signal representative of the change in origin of the yarn from said first bobbin to said second bobbin when said first presence signals terminate and said second presence signals commence.

13. A method as claimed in claim 12, further comprising generating by means of said control unit a stop signal representative of the absence of yarn in the passage section if reception of said first and second presence signals is absent.

14. A method as claimed in claim 12, further comprising generating by means of said control unit an irregularity signal representative of the simultaneous reception of said first and second presence signals.

15. A device as claimed in claim 2, further comprising change-over notification means operatively associated with the control unit to acquire said change-over signal and/or the stop signal and to generate a corresponding electrical, acoustic and/or visual warning signal.

16. A device as claimed in claim 8, further comprising a thread guide member disposed between the arms and at least partly defining said passage section; said thread guide member being of substantially annular shape.

17. A device as claimed in claim 8, further comprising a thread guide member disposed between the arms and at least partly defining said passage section; said thread guide member being of substantially annular shape and made of ceramic material.

18. A device as claimed in claim 1, further comprising a connection for connecting said device to a textile machine, by means of a serial line, to programme at least one operating parameter and/or to read an intercepted state or event to save at least one information item in order to enable traceability of the finished product on the basis of the bobbin of origin.

* * * * *